United States Patent
Kallmes (10) Patent No.: US 7,779,685 B2
(45) Date of Patent: *Aug. 24, 2010

(54) FLUID TRANSPORTATION BY A SHEET OF MATERIAL

(76) Inventor: Andrew Kallmes, 10319 Westlake Dr., #164, Bethesda, MD (US) 20817

( * ) Notice: Subject to any disclaimer, the term of this patent is extended or adjusted under 35 U.S.C. 154(b) by 82 days.

This patent is subject to a terminal disclaimer.

(21) Appl. No.: 12/147,637

(22) Filed: Jun. 27, 2008

(65) Prior Publication Data

US 2009/0158825 A1    Jun. 25, 2009

Related U.S. Application Data

(60) Provisional application No. 60/946,707, filed on Jun. 27, 2007.

(51) Int. Cl.
*G01L 5/04* (2006.01)
(52) U.S. Cl. .......................................... 73/159
(58) Field of Classification Search .................. None
See application file for complete search history.

(56) References Cited

U.S. PATENT DOCUMENTS

| | | | | |
|---|---|---|---|---|
| 2,294,511 A | * | 9/1942 | Neiman | 73/38 |
| 5,069,065 A | * | 12/1991 | Sprunt et al. | 73/152.09 |
| 2009/0241640 A1 | * | 10/2009 | Kallmes | 73/38 |

* cited by examiner

*Primary Examiner*—Robert R Raevis
(74) *Attorney, Agent, or Firm*—Louis L. Wu (57) ABSTRACT

Apparatuses and methods are provided for transporting fluid to a sheet of material. Typically, the sheet is immobilized on an upper surface of a support structure. A container holding a fluid is provided along with a conduit having a fluid-conveying lumen that extends from the container to one or more terminal opening facing the lower surface of the sheet. Optionally, a porous medium is placed in fluid communication with the fluid-conveying lumen and in contact with the lower surface of the sheet. The apparatuses and methods provide a variety of interfaces that facilitate controlled fluid transportation from the lumen against gravity for absorption by the sheet.

24 Claims, 6 Drawing Sheets

FIG. 6B

FLUID TRANSPORTATION BY A SHEET OF MATERIAL

CROSS REFERENCE TO RELATED APPLICATIONS

This application claims priority to U.S. Provisional Patent Application Ser. No. 60/946,707, filed Jun. 27, 2007, entitled "Fluid Transportation by a Sheet of Material," by Andrew Kallmes, the disclosure of which is incorporated by reference in its entirety.

BACKGROUND

1. Field of the Invention

The invention relates generally to apparatuses and methods for measuring the fluid transportation and/or absorption behavior of sheet materials.

2. Description of Related Art

The desirability and performance characteristics of numerous sheet materials depend in large part on their fluid-transportation and/or absorption behavior. For example, paper towels, tissues, and other cellulosic sheets are often evaluated by their ability to absorb water and fluids containing liquid water. Similarly, a number of fabrics have been developed for their ability to absorb and wick moisture from a surface, e.g., wick perspiration from skin. Examples of such fabrics include a weft knits, denier gradient textiles and assorted laminates such as those described in U.S. Pat. No. 5,735,145 to Pernick and U.S. Pat. No. 5,021,280 to Farnworth et al.

There are presently several methods and apparatus for determining the fluid-transportation properties of materials. For example, U.S. Pat. No. 5,138,870 to Lyssy describes an apparatus for measuring the water vapor permeability of sheet materials under adjustable constant measuring conditions. A lid having an air inlet opening and an outlet opening is attached on a cup containing water in a vapor and airtight manner. A sheet material having its circumferential border held between the rims of the cup and lid separates the water in the cup from the lid. An absorption member containing a moisture-absorbent material is in communication with the outlet opening. A blower in communication with the air inlet opening aspirates air through an air dryer and blows the resulting dry air into the sealed cup containing the sheet material. As a result, the permeability of the sheet material may be measured.

For liquid absorption testing, U.S. Pat. No. 4,357,827 to McConnell describes a gravimetric absorbency tester that determines the wicking properties of a material by determining the weight of liquid flowing to or from a test site. The apparatus includes a vessel for containing liquid supported solely by a balance, an indicator for indicating the weight sensed by the balance, a test surface containing the test site on which a specimen to be tested may received, a conduit operatively connecting the vessel to the test site for directing a flow of liquid between the vessel and test site, and an adjuster for vertically positioning the test site. The surface of the liquid in the vessel is maintained at a constant elevation as liquid flows into and out of the vessel.

One problematic issue associated with generally all liquid absorption testing involves the interface through which liquid is introduced into the specimen. For example, when the technology described in U.S. Pat. No. 4,357,827 to McConnell is used, the test specimen is placed on a test plate having a hole though which liquid may be directed in an upward direction toward the specimen. This is problematic because fluid may preferentially wick along in the boundary between the specimen and the test plate instead of being absorbed the test specimen. In addition, a means may be required to provide sufficient activation energy to induce the liquid from the hole to wet the specimen and to liquid absorption by the specimen. Such means may, for example, include a pinch valve that allows liquid to be forced through the hole at a velocity that allows the liquid to contact the specimen and overcome surface forces against wetting. Such means may compromise tests designed to measure the intrinsic absorption properties of the test specimen because they introduce excess measurement noise.

Another problematic issue associated liquid absorption testing is that test specimens may swell and/or deform as they absorb liquid. As a result, the test specimens in part or in whole may be displaced relative to the surface from which test specimens absorb liquid during testing. In turn, liquid transport behavior may be disrupted or otherwise altered, thereby compromising the accuracy of the test.

Accordingly, there exist opportunities to provide alternatives and improvements to known methods and apparatuses for determining the fluid-transportation properties of materials, particularly for the purpose of overcoming any shortcomings associated with known methods and apparatuses.

SUMMARY OF THE INVENTION

Apparatuses and methods are provided for transporting fluid to a sheet of material. Typically, the sheet is immobilized on an upper surface of a support structure. The upper surface of the support structure may be bounded by a periphery and may contact a minority portion, e.g., no more than 10% of a lower surface of the sheet within the periphery. A container holding a fluid is provided along with a conduit having a fluid-conveying lumen that extends from the container to one or more terminal opening facing the lower surface of the sheet. Optionally, a porous medium is placed in fluid communication with the fluid-conveying lumen and in contact with the lower surface of the sheet. The medium has wetting properties effective to allow the fluid to be wicked from the lumen against gravity via capillary action. Once transported to an upper surface of the porous medium, the sheet absorbs the fluid from the medium. By measuring the fluid transported from the container, fluid-transport and/or absorption properties of the sheet may be assessed.

In another embodiment, an assembly for wetting a sheet of material is provided. The assembly includes a sheet of material supported by a support structure as described above. A means for immobilizing the sheet on support structure, e.g., a weight having substantially coplanar lower exterior and interior surfaces, may be placed in contact with the upper surface of the sheet.

In still another embodiment, the invention provides a method for assessing fluid-transportation anisotropy by a sheet of material having an upper surface and a lower surface. The method involves obtaining data from a first absorption test that employs a single wetting interface at a lower surface of a first test sheet of the material and obtaining data from a second absorption test that employs a plurality of wetting interfaces at a lower surface of a second test sheet of material. The data for the first and second absorption tests are compared to determine any differences between radial and axial fluid-transporting behavior the sheet of the material over time, optionally relative to saturation.

In a further embodiment, an apparatus is provided for transporting fluid to a sheet of material as generally described above but with a means for positioning an interfacing portion of the sheet to absorb fluid through the opening. Such positioning means may include, for example, a member for controllably pressing the interfacing portion of the sheet through the opening. The member may includes a screw that has spiral grooves that allows for controllable positioning of the member relative to the weight on the sheet.

In a still further embodiment, a method is provided wherein a sheet is in a horizontal orientation on upper surface of a support. Fluid is directed from a container through a fluid-conveying lumen of a conduit that extends from the container to a terminal opening facing the lower surface of the sheet such that a negative head is defined between the lower surface of the sheet and the fluid in the opening. An interfacing portion of the sheet is lowered to absorb fluid through the opening against gravity.

BRIEF DESCRIPTION OF THE DRAWINGS

FIGS. 1A and 1B, collectively referred to as FIG. 1, depict simplified embodiments of the invention in the form of apparatuses that use a porous medium for wicking fluid upward via capillary action to evaluate fluid transportation properties of a sheet of material in a horizontal orientation.

FIGS. 2A, 2B, and 2C, collectively referred to as FIG. 2, depict a web plate and a porous sheet of material suitable for use as the sample holder of the invention.

FIGS. 3A, 3B, and 3C, collectively referred to as FIG. 3, depict a prior art support plate that contacts greater than a majority of a lower sheet surface.

FIGS. 4A, 4B, 4C, and 4D, collectively referred to as FIG. 4, depict a weight suitable for use with the invention.

FIGS. 6A and 6B, collectively referred to as FIG. 6, depict a simplified embodiment of the invention in the form of an apparatus that use a center screw to position an interfacing portion of a sheet in a controllable manner so as to evaluate fluid transportation properties of a sheet of material.

DETAILED DESCRIPTION OF THE INVENTION

Before describing the present invention in detail, it is to be understood that the invention is not limited to specific fluids or porous media, as such may vary. It is also to be understood that the terminology used herein is for describing particular embodiments only, and is not intended to be limiting.

In addition, as used in this specification and the appended claims, the singular article forms "a," "an," and "the" include both singular and plural referents unless the context clearly dictates otherwise. Thus, for example, reference to "an opening" includes an arrangement of openings as well as a single opening, reference to "fluid" includes a single fluid as well as a mixture of fluids, and the like.

In this specification and in the claims that follow, reference will be made to a number of terms that shall be defined to have the following meanings, unless the context in which they are employed clearly indicates otherwise:

The term "array" is used herein in its ordinary sense and refers to an ordered arrangement of features, e.g., holes, in one, two, or three dimensions, e.g., rectilinear grids, parallel stripes, spirals, and the like.

The terms "cellulose, "cellulosic" and the like are used herein in their ordinary sense and refer to a complex carbohydrate or polysaccharide that includes a plurality of monomeric glucose units ($C_6H_{10}O_5$). As is well known in the art, cellulose constitutes the chief part of the cell walls of plants, occurs naturally in fibrous products such as cotton and linen, and is the raw material of many manufactured goods such as paper, rayon, and cellophane.

The term "fluid" is used herein in its ordinary sense and refers to matter that is nonsolid or at least partially gaseous and/or liquid. A fluid may contain a solid that is minimally, partially or fully solvated, dispersed or suspended. Examples of fluids include, without limitation, aqueous liquids (including water per se and salt water) and nonaqueous liquids such as organic solvents and the like.

The term "head" refers to the relative positions between a fluid source and a support on which an interfacing portion of a sheet may be placed to absorb fluid from the source. A "negative head" refers to an arrangement in which the sheet does not absorb fluid without from the source in the absence of added activation energy to initiate absorption.

The term "substantially identical" as used to describe a plurality of items indicates that the items are identical to a considerable degree, but that absolute identicalness is not required. For example, when openings are described herein as of a "substantially identical size," the openings' size may be identical or sufficiently near identical such that any differences in their size are trivial in nature and do not adversely affect the performance of the openings' function. The terms "substantial" and "substantially" are used analogously in other contexts involve an analogous definition.

In general, the invention relates to apparatuses for measuring wetting and/or other mechanisms of fluid transportation by a sheet of material. Typically, the sheet has upper and lower surfaces and is immobilized on an upper surface of a support structure. A container holding a fluid is provided with a conduit having a fluid-conveying lumen that extends from the container to a terminal opening facing the lower surface of the sheet. The sheet is positioned to absorb fluid from the terminal opening. A means may be provided for measuring and/or monitor the amount of fluid in the container to determine the fluid-transportation or absorption properties of the sheet.

Typically, the invention is practiced in a manner that provides an accurate means for determining the intrinsic fluid-transporting properties and behavior of the sheet. In contrast to prior art technologies, the invention minimizes systemic measurement error, e.g., those that may arise through the inappropriately forceful introduction of fluid into the sheet. That is, the invention provides a means to deliver fluid for absorption by a sheet at a rate that matches the intrinsic transporting rate of the sheet. In some embodiments, a "controlled puddle" is provided from which a sheet interfaced therewith may absorb fluid in a manner such that fluid-transport dynamics are overwhelming dominated by the intrinsic properties of the sheet rather than by the manner in which fluid is initially delivered to the sheet. In other embodiments, a means is provided to ensure that only an interfacing portion of the sheet is controllably lowered and maintained in position to absorb fluid from the terminal opening.

The invention may be practiced to ensure the intrinsic properties of the sheet dominate the dynamics of fluid-transportation. For example, the inventive apparatus may be constructed such that the upper surface of the support structure is bounded a periphery and contacts a minority portion (e.g., no more than about 5% to about 10%) of the lower surface of the sheet within the periphery. Optionally, a porous medium is placed in fluid communication with the fluid-conveying lumen and in contact with the lower surface of the sheet. The medium may have wetting properties effective to allow the medium to wick fluid from the lumen against gravity via capillary action and to allow the sheet to absorb the fluid from the medium.

Figure 1A:
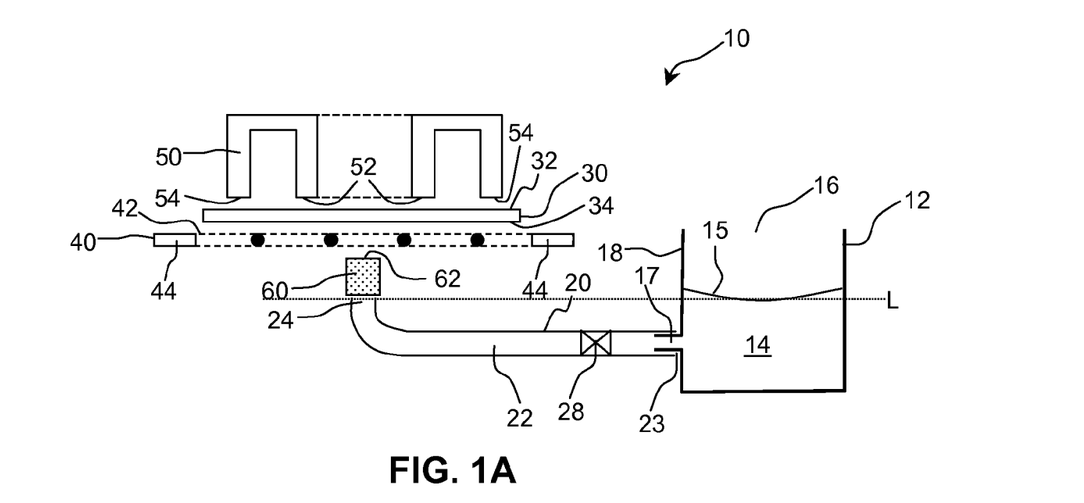
FIG. 1A shows in schematic cross-sectional exploded view an embodiment wherein a conduit is connected to an outlet port extending through a submerged portion of a container of liquid.
Figure 1B:
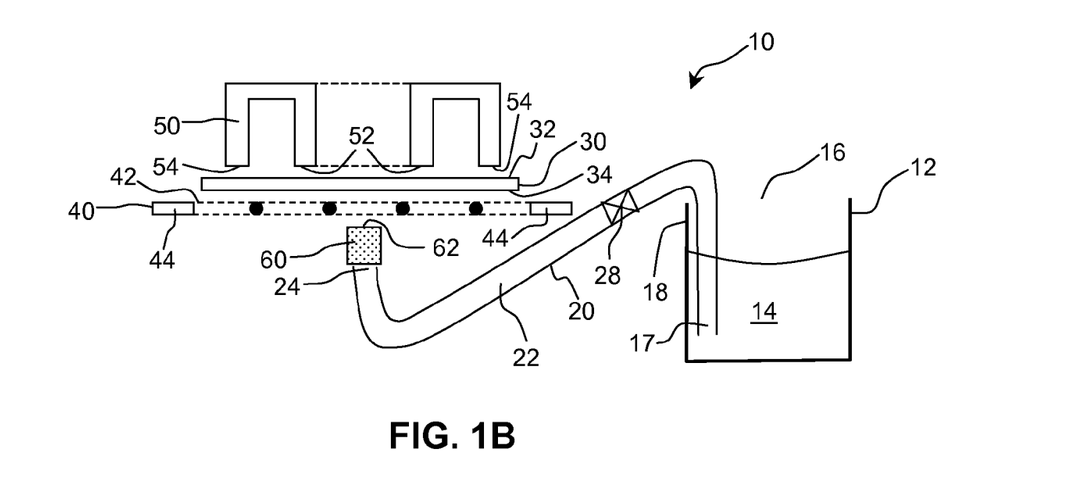
FIG. 1B shows in schematic cross-sectional exploded view an embodiment wherein the conduit is arranged in manner that requires a siphoning action to transport liquid over the top of the container.
Figure 2A:
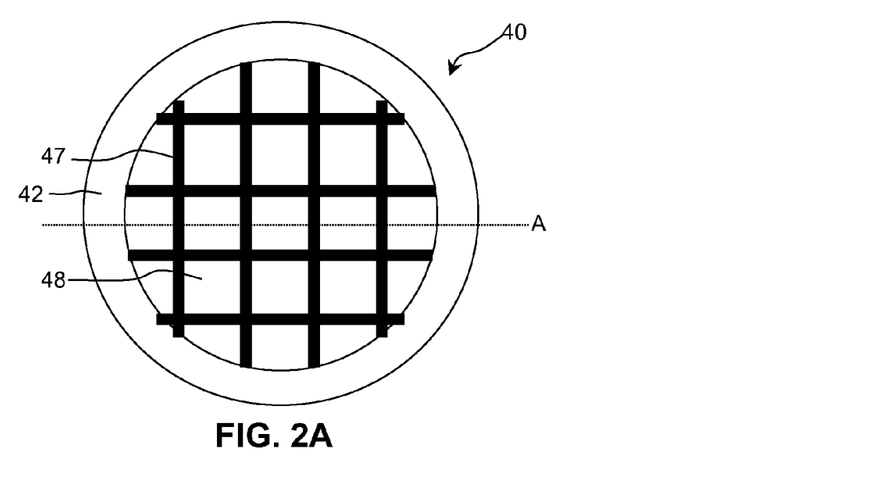
FIG. 2A shows the web plate in simplified schematic top view.
Figure 2B:
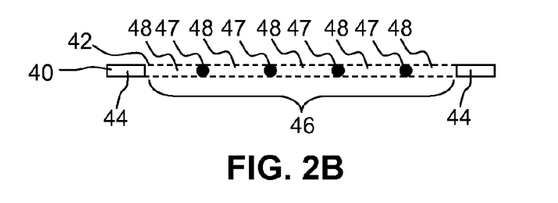
FIG. 2B shows a simplified schematic cross-sectional view of the web plate along a plane indicated by dotted line A with a porous sheet on an upper surface thereof.
Figure 2C:
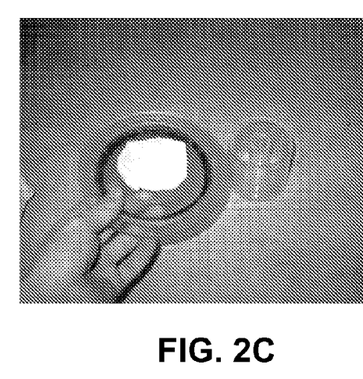
FIG. 2C is a photograph of an exemplary web plate having a sheet on an upper surface thereof held next to an optional weight.
Figure 2D:
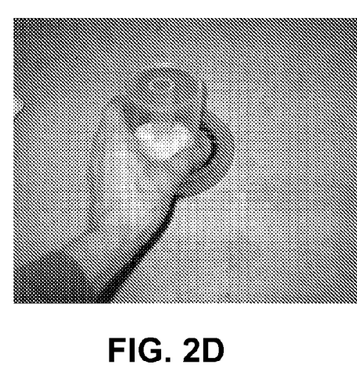
FIG. 2D is a photograph of the same web plate and sheet with the weight held over the sheet.

A simplified exemplary embodiment of the inventive apparatus is schematically depicted in FIG. 1. As with all figures referenced herein, in which like parts are referenced by like numerals, FIG. 1 is not necessarily to scale, and certain dimensions may be exaggerated for clarity of presentation. Referring to FIG. 1, the apparatus 10 includes a container 12 which acts as a reservoir that holds or serves as a source of a liquid 14 to be employed in testing the performance of a suitable sample sheet 30 of material. As shown, the container 12 has an upper opening 16 through which liquid 14 may be added.

Also shown is a conduit 20 having a fluid-conveying lumen 22 that extends from a first terminal opening 23 at or near a submerged portion of the container 12 to a second terminal opening 24. The conduit may transport liquid from the container in various ways. In FIG. 1A, for example, the first terminal opening 23 of the conduit is connect to a port 17 extending through a container wall 18 and located at a submerged portion of the container 12. In contrast, as shown in FIG. 1B, the conduit 20 may extend in a configuration that allows liquid 14 to be siphoned from a first terminal opening 23 upward through upper opening 16 of the container 12 and over the top of container wall 18. Preferably, liquid 14 is siphoned for the apparatus shown in FIG. 1B in a manner that does not trap any air or other gas pockets in the conduit lumen 22.

The sheet 30 has an upper surface 32 and a lower surface 34 and is interposed in a horizontal orientation between a support structure 40 and a means for immobilizing the sheet in the form of a weight 50 placed on the upper surface 32 of the sheet 30. As shown, the weight 50 may have a lower interior surface 52 and a lower exterior surface 54 that contacts the upper surface 32. The support structure 40 has an upper surface 42 bounded by a periphery 44. As discussed in detail below, the support structure 40 may include a web plate having an upper surface 42 that contacts no more than 10% of the lower sheet surface 34 within the periphery 44.

The second terminal opening 24 of the lumen 22 is positioned in facing relationship to the lower surface 34 of the sheet 30. Typically, the opening 24 is positioned at a height such that it lies in horizontal plane "L," as generally defined by the meniscus surface 15 of the liquid 14 in the reservoir vessel 12. Care must be taken in positioning opening 24 relative to plane L. If the opening 24 is elevated relative to plane L, a means may be required to provide sufficient activation energy to induce the liquid from the hole to wet the sheet 30. However, if the opening 24 is located below plane L, liquid will tend to flow out of opening 24.

A porous medium 60 is placed in fluid communication with the lumen 22. As a result, the medium 60 extends from terminal opening 24, and an upper surface 62 of the medium 60 contacts the lower surface 34 of the sheet 30. Notably, the medium 60 contacts a portion of the sheet 30 generally bounded by lower interior surface 52 of the weight. The medium 60 has wetting properties effective to allow for liquid 14 to be wicked upward via capillary action toward the sheet 30.

In operation, the sheet 30 to be tested is placed on the top surface 42 of the support structure. The weight 50 is placed on the sheet 30 so that both lower surfaces 52 and 54 contacts the upper sheet surface 32. As the terminal opening 24 is positioned in substantially the same level as the surface 15 of the liquid 14 in the container 12, liquid 14 is free to flow from the container 12 to terminal opening 24 due to gravitational forces when valve 28 in the conduit 20 is opened. The porous medium 60 wicks liquid 14 from the opening 24 of the lumen 20 against gravity via capillary action toward surface 62, thereby effectively providing a controlled puddle.

Then, sheet 30 then absorbs liquid 14 from the container 12. Typically, the container 12 holds a sufficiently large volume of liquid such that the level of the surface 15 does not substantially change while liquid 14 is absorbed by the sheet 30. That is, the porous medium 60 may serve as a "controlled puddle" interface to an effectively limitless amount of liquid for absorption by the sheet 30. If however, a smaller amount of liquid is used, a mechanism may be used to maintain relative height of the opening 24 and the liquid surface 15 in the container 12.

By monitoring the quantity of liquid in the container 12 before any liquid 14 has flowed from the container 12 to the sheet 30, and the weight after all absorption by the sheet 30 has ceased, the total amount of liquid taken up by the test sheet 30 may then be determined. The apparatus can also be employed to evaluate the absorbency rate of a specimen by noting the change in the amount of liquid in the container over a period of time.

In other words, a method is provided for transporting fluid for absorption by a sheet of material having an upper surface and a lower surface. The sheet is placed in a horizontal orientation on upper surface of a support such that the upper surface of the support structure contacts no more than 10% of the lower surface of the sheet within a periphery bounding the upper surface. Fluid is directed from a container through a fluid-conveying lumen of a conduit that extends from the container to a terminal opening facing the lower surface of the sheet. A porous medium in fluid communication with the fluid-conveying lumen and in contact with the lower surface of the sheet is allowed to wick fluid from the lumen against gravity via capillary action and to allow the sheet to absorb the fluid from the medium. Optionally, the fluid in the container is measured repeatedly while the fluid flows through the lumen and/or the porous medium.

FIG. 2 shows in detail the web plate 40 suitable for use with the invention. As shown in FIG. 2A, the web plate includes a central web section 46 formed from a plurality of regularly-spaced intersecting filaments 47 defining an array of through opening 48 of substantially identical size and shape. As shown in FIG. 2B, the filaments 47 may be stretched under tension, be bounded by periphery 44, and define a substantially planar upper horizontal surface. Optionally, filaments are interlaced. When a sheet 30 is placed on the upper surface 42 of the web plate 40, only a small portion, e.g., less than 5% to 10%, of the lower sheet surface 34 contacts the web section 46, since the web section 46 area may include a greater portion of openings 48 than filaments 47. As a result, only a small amount of fluid may collect about the boundary between the web plate 40 and the sheet.

Figure 3A:
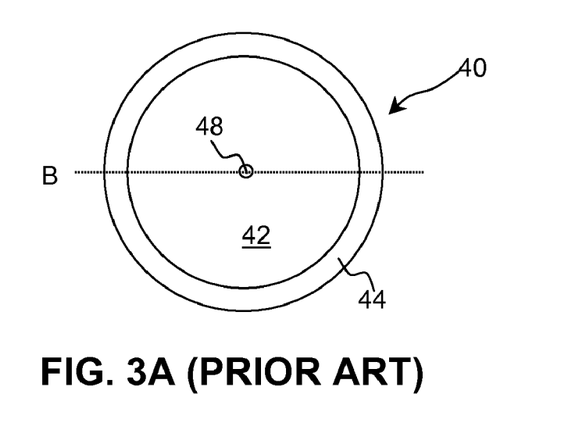
FIG. 3A schematically shows in top view the support plate without a sheet on an upper surface thereof.
Figure 3B:
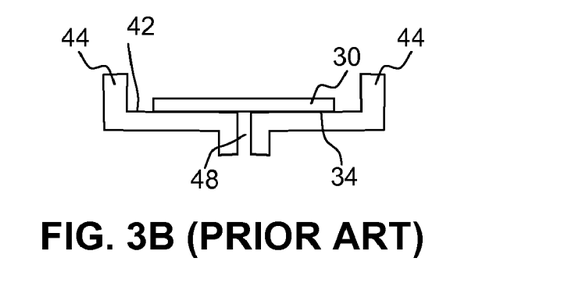
FIG. 3B shows in cross-sectional schematic view the support plate along a plane indicated by dotted line B with a sheet on an upper surface thereof.
Figure 3C:
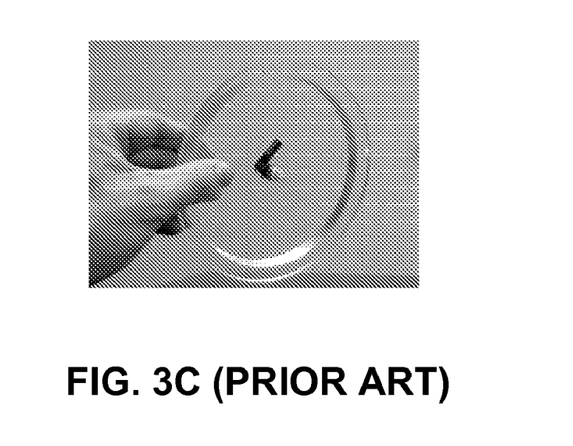
FIG. 3C is a photograph of a prior art support plate.
Figure 4A:
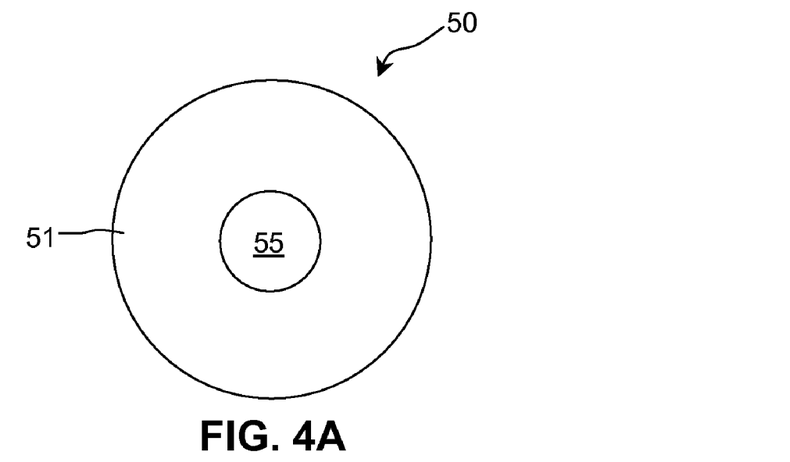
FIG. 4A schematically shows the weight in top view.
Figure 4B:
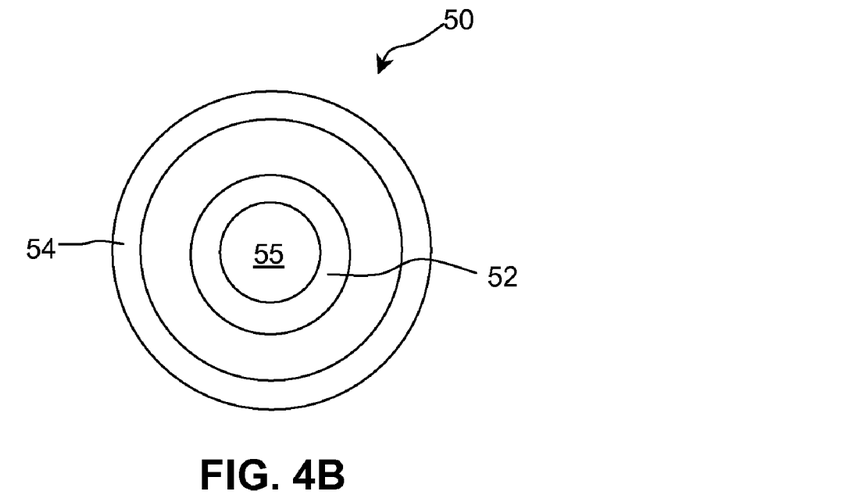
FIG. 4B schematically shows the weight in bottom view.
Figure 4C:
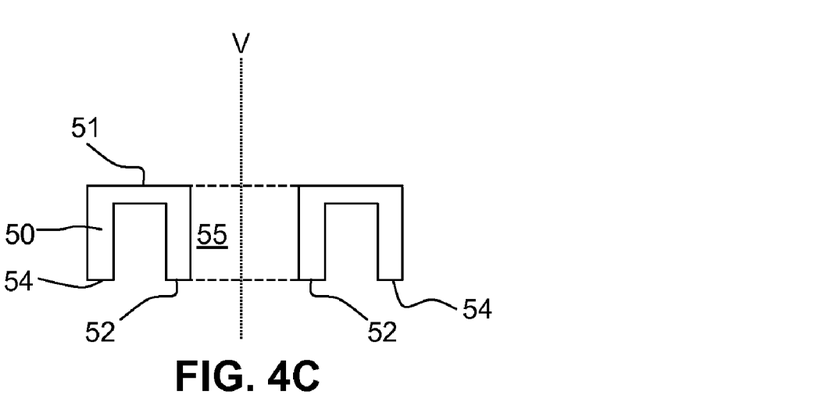
FIG. 4C schematically shows the weight in cross sectional view along a plane indicated by dotted line C.
Figure 4D:
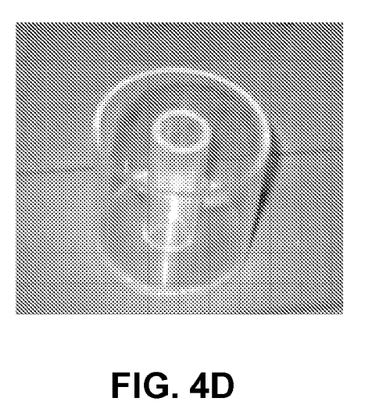
FIG. 4D is a photograph or an exemplary weight similar to that depicted in FIGS. 4A-4C.

In contrast, FIG. 3 shows a prior art support plate 40 that includes a central opening 48 through which liquid may be introduced to the upper support plate surface 42. When a sheet 30 is placed on the upper support plate surface 42, substantially then entirety of the lower sheet surface 34 faces the upper support plate surface 42. As a result, fluid may pool or preferentially wet the boundary between the lower sheet surface 34 and the upper support plate surface 42. As boundary fluid does not represent fluid transported solely as a result of the intrinsic absorption properties of the sheet, sheet absorption measurements may be compromised.

FIG. 4 depicts a weight 50 that may be used as means for immobilizing the sheet on the upper support structure surface 42. As shown, the weight 50 may be comprised of a unitary piece having an upper surface 51, and coplanar lower interior and exterior surfaces 52 and 54. A through hole 55 extends along vertical axis V through the weight and provides communication between the upper surface 51 and the lower interior surface 52. The lower surfaces are substantially concentric about axis V, which perpendicular to the plane of the lower surfaces.

When placed in operation, as shown in FIG. 1, the weight 50 is placed on the upper sheet surface 32. The lower weight surfaces 52 and 54 serve to maintain the substantial planarity of the sheet as the sheet is wet. Accordingly, the weight may comprise or be coated with a hydrophobic material, e.g., silicones, fluorinated and perfluorinated polymers, polyolefins, certain acrylics, etc., at and/or near the lower interior surface of the weight. In any case, the through hole 55 allows an operator of the invention to view the initial wetting of the sheet 30.

Thus, in another embodiment, an assembly for wetting a sheet of material is provided. That includes a sheet of material supported by a support structure as described above. A weight having substantially coplanar lower exterior and interior surfaces is placed in contact with the upper surface of the sheet.

The invention may be used with any of a number of fluids. Typically, the invention is used in combination with liquids, but fluids such as emulsions, suspension, etc. may also be compatible with the invention. In particular, the invention finds widespread use in combination with aqueous fluids, e.g., a water-based saline solutions, though nonaqueous and/or organic fluids may be suitable for use with the invention.

The porous medium may vary as well. Typically, the porous medium is substantially incompressible and may comprise a glass frit material. However, the porous medium may be compressible in some situations. For example, the porous medium may additionally or alternatively comprise a sponge or other porous disposable material suitable for wicking fluid toward the sample. Disposable materials are well suited for samples that include fluid soluble components that may flow into the porous medium.

Depending on the requirements of the practitioner of the invention, the porous medium may be effective to transport the fluid from the lumen to a distance of at least about 3 to 5 millimeters upward against gravity via capillary action. In addition, the overall construction of the medium may vary as well. For example, the porous medium may have a surface facing the sheet with an area of at least about 1 $cm^2$ or about 2 $cm^2$ to about 4 $cm^2$. An exemplary medium for use with the invention may have a porosity of at least about 30% and a pore size and surface properties appropriate for wicking the test fluid.

Any number of means may be used for measuring fluid in the container. For example, the fluid may be measured by weight. In some instances, the container may be supported solely by a weight sensing surface of a weighing means such as an electronic balance having a tare switch and a display. If desired, a force transducer or similar device may be used instead of a balance. In addition or in the alternative, optical and/or electronic means may be used to measure the volume of the fluid in the container. Additional fluid measuring means may include flow meters and other devices effective to measure and/or monitor a change in the fluid content in the container over a desired time period.

The invention may be used with any of a number of sheet materials. For example, the sheet may be at least cellulosic in part, e.g., a paper product. In addition or in the alternative, the sheet may comprise one or more synthetic polymeric materials such as polyesters, polyamides, polyurethanes, polyethylene glycols, acrylic polymers, combinations thereof, and copolymers of any of the foregoing. In some instances, sheets such as woven, laminate, and/or denier gradient fabrics may be used. Such so-called "high-performance wicking" fabrics may be used with or without chemical treatment in apparel that allows moisture to be transported away from a wearer, thereby balancing body temperature and enhancing comfort.

To measure the performance of such "high-performance wicking fabrics," it is often necessary to approximate such fabrics in use, e.g., as exercise apparel. Since exercise apparel are often used in varying operating conditions, the invention may include additional features to simulate these operating conditions. For example, a means may be provided for increasing vapor transport at the upper surface of the sheet. Such vapor-transport-increasing means may includes a blower and/or a suction device, e.g., to approximate wind conditions a runner might experience. Similarly, a means may be for transporting fluid through the conduit at a predetermined rate, e.g., selected to approximate human perspiration. Such means may include a pump, suction device, and/or other fluid-transporting devices known in the art.

When the inventive apparatus includes a conduit having a fluid-conveying lumen that extends from the container to plurality of terminal openings facing the lower surface of the sheet, the porous material may sometimes be omitted. The terminal openings may form an array, e.g., a circular array. The openings are may vary or be substantially identical in size and/or shape. When each opening has a circular shape, their diameters may range from about 0.5 to about 6 mm, or more specifically, from about 2 to about 4 mm.

In still another embodiment, the invention provides a method for assessing fluid-transportation anisotropy by a sheet of material having an upper surface and a lower surface. The method involves obtaining data from a first absorption test that employs a single wetting interface at a lower surface of a first test sheet of the material and obtaining data from a second absorption test that employs a plurality of wetting interfaces at a lower surface of a second test sheet of material. The data for the first and second absorption tests are compared to determine any differences between radial and axial fluid-transporting behavior the sheet of the material over time.

Figure 5:
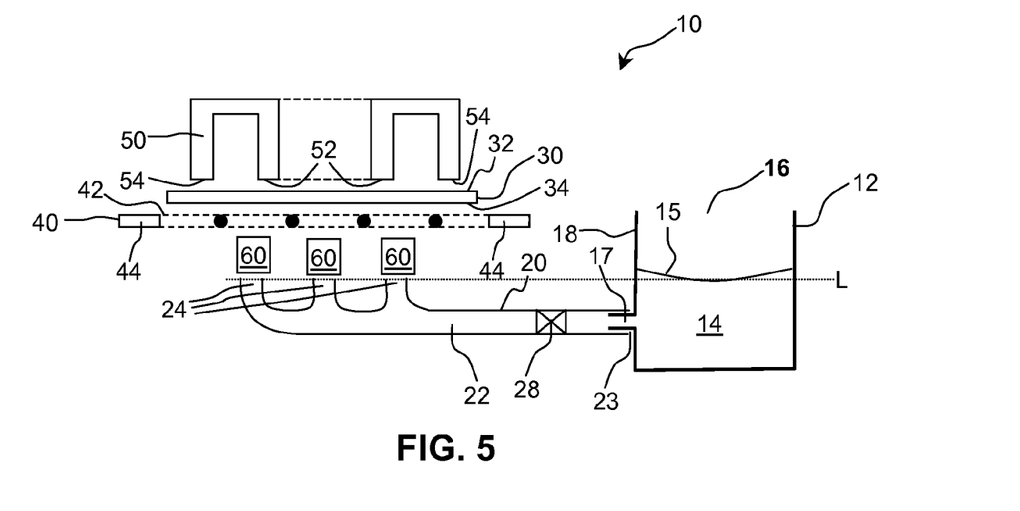
FIG. 5 schematically depicts a simplified embodiment of the invention in the form of an apparatus similar to that shown in FIG. 1A except a plurality of porous media is provided, each in communication with a different terminal opening.

For example, a first absorption test may be carried out using an apparatus that includes a first test sheet and single wetting interface as shown in FIG. 1A. A second absorption test may be carried out using a second test sheet substantially identical to the first test sheet and a plurality of wetting interfaces as shown in FIG. 5. If all wetting interfaces are substantially identical, the initial uptake rate of the second test sheet should be proportional to the initial uptake rate of the first test sheet by the number of wetting interfaces used in the second test.

However, it should be also be apparent that the second sheet should be saturated more quickly than the first sheet. In addition, wetting of the first sheet is accomplished through a more horizontal (radial) absorption mechanism, while a more vertical (axial) absorption mechanism controls the wetting of the second sheet. Thus, by comparing the data of the two tests, those of ordinary skill in the art should be able to assess any differences between directional absorption properties of the sheets.

FIG. 6 depicts another simplified embodiment of the inventive apparatus having some similarity to that shown in FIG. 1A. For example, the apparatus of FIG. 6 include a container 12 and a conduit 20 having a fluid-conveying lumen 22 that extends from a first terminal opening 23 to a second terminal opening 24 that faces support structure 40. Like the conduit shown in FIG. 1A, the conduit 20 of FIG. 6 serves to transport liquid 14 from the container 12 test sample sheet 30, which is interposed in a horizontal orientation between a support structure 40 and weight 50. However, the apparatus of FIG. 6 does not include a porous medium between the conduit and the sample.

The weight 50 of FIG. 6 is also similar to that shown in FIG. 4 except that it includes a guide 57 spanning across hole 55 that engages a single screw 58 centered therein. The screw 58 may be lowered or raised relative to the guide 57 and other parts of the weight 50 by turning the screw clockwise or counterclockwise, respectively. As a result, the movable screw 58 may serve as a means for positioning or maintaining the position of an interfacing portion 35 of the sheet to absorb fluid through opening 24.

FIG. 6 shows that terminal opening 24 of the lumen 22 is positioned in facing relationship to the lower surface 34 of the sheet 30 at a height slightly above horizontal plane "L" which is defined by surface 15A of the liquid 14 in the reservoir vessel 12. Accordingly, at equilibrium, liquid 14 forms a surface 15B that lies slightly below opening 24. That is, meniscus surfaces 15A and 15B both generally lie in plane L.

Figure 6A:
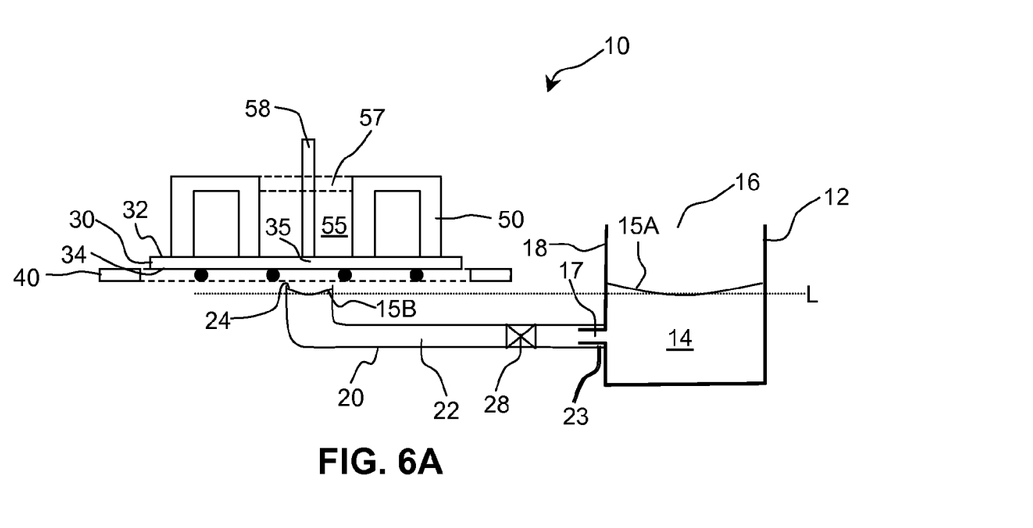
FIG. 6A shows in schematic cross-sectional view the embodiment that exhibits a negative head arrangement that prevents the sheet from absorbing fluid through a terminal opening of the conduit.

In operation, as shown in FIG. 6A, a sheet 30 to be tested is placed on the support structure 40. The weight 50 is placed on the upper surface 32 of sheet 30. As a result, the sheet is rendered substantially immobile on the support structure.

As shown in FIG. 6A, sheet 30 does not contact meniscus surface 15B. That is, FIG. 6A depicts a negative head arrangement. Typical negative head arrangements may be such that the opening or liquid meniscus is located at least about one to about ten millimeters below the support structure and/or the sheet.

In general, when prior art negative-head liquid-absorption sheet testing equipment is used, testing may require one or both of two approaches to initial liquid absorption. The first approach is to force or squirt liquid upward into the sample sheet on a support using a pinch valve or the like. The second approach is to lower the support to directly into the liquid to be absorbed. Both approaches tend to produce excessive momentum-related artifacts that skew test data.

Figure 6B:
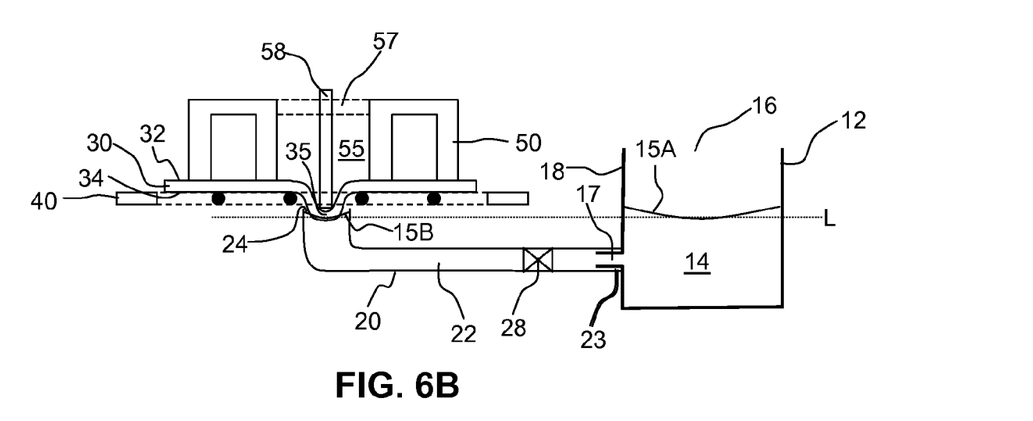
FIG. 6B shows in schematic cross-sectional view the embodiment wherein the center screw is used to depress the interfacing portion of the sheet into the conduit to absorbing fluid through the terminal opening.

In contrast, as shown in FIG. 6B, the invention may involve the use of the center screw to deform the sample sheet 30 or manipulate only a portion of the sample sheet on the support structure 40 to initiate absorption. As shown in FIG. 6B, the center screw 58 is slowly turned so that is it presses gently downward against the 32 upper surface of the sheet's interfacing portion 35. As a result, at least the lower surface 34 of the sheet's interfacing portion 35 travels through opening 24. When the sheet's interfacing portion 35 breaks meniscus 15B and effectively becomes submerged in liquid 14 in lumen 12, sufficient activation energy has been provided to allow the sheet 30 to begin absorbing liquid. In effect, the screw 58 serves as a means to ensure the establishment and maintenance of a single point interface between the sample sheet and the liquid. Those of ordinary skill in the art will recognize that the invention allows for a greater initial negative head than known absorption testing technologies.

Thus, the invention provides a number of advantages over known absorption testing equipment and methods. In general, the invention provides an improved interface through which liquid may be introduced into the specimen for the duration of absorption testing. The improved interface may serve to: (1) reduce the activation energy required for initiating absorption testing; (2) maintain contact between the liquid to be absorbed with the sheet to be tested; (3) allow for a greater negative head; and (4) improve the repeatability of results.

Variations of the present invention will be apparent to those of ordinary skill in the art in view of the disclosure contained herein and may be discovered upon routine experimentation. For example, while the a center screw has been disclosed herein as a means for positioning an interfacing portion of the sheet to absorb fluid through the opening against gravity member, other means may be used as well. In some instances, the means may include levers, gears, pulleys, etc., in addition to or instead of spiral grooves to allow controllable positioning of the sheet's interfacing structure. Similarly, various vertical leveling mechanism known in the art may be used in conjunction with the support structure.

It is to be understood that, while the invention has been described in conjunction with the preferred specific embodiments thereof, the foregoing description merely illustrates and does not limit the scope of the invention. Numerous alternatives and equivalents exist which do not depart from the invention set forth above. For example, the inventive apparatus may be constructed to contain or exclude specific features and components according to the intended use of the apparatus, and any particular embodiment of the invention, e.g., those depicted in any drawing herein, may be modified to include or exclude element of other embodiments. Alternatively, stated, different features of the invention described above may be combined in different ways. Other aspects, advantages, and modifications within the scope of the invention will be apparent to those skilled in the art to which the invention pertains.

All patents disclosed herein are incorporated by reference in their entirety to an extent not inconsistent with the above disclosure.

I claim:

1. An apparatus for transporting fluid to a sheet having an upper surface and a lower surface in a horizontal orientation, comprising:

a support structure having an upper surface bounded by a periphery and supporting the sheet, wherein the upper surface of the support structure contacts no more than 10% of the lower surface of the sheet within the periphery;

a means for immobilizing the sheet on support structure;

a container holding a fluid;

a conduit having a fluid-conveying lumen that extends from the container to a terminal opening facing the lower surface of the sheet; and a porous medium in fluid communication with the fluid-conveying lumen and in contact with the lower surface of the sheet, the medium having wetting properties effective to allow the medium to wick fluid from the lumen against gravity via capillary action and to allow the sheet to absorb the fluid from the medium.

2. The apparatus of claim 1, wherein the support structure contacts no more than about 5% of the lower surface of the sheet.

3. The apparatus of claim 1, wherein the support structure comprises a web plate.

4. The apparatus of claim 1, wherein the container includes an opening at a lower portion thereof through which fluid is conveyed via the fluid-conveying lumen to the porous medium.

5. The apparatus of claim 1, wherein the fluid comprises liquid water.

6. The apparatus of claim 1, wherein the porous medium is substantially incompressible.

7. The apparatus of claim 6, wherein the porous medium comprises a glass frit material.

8. The apparatus of claim 1, further comprising a means for measuring fluid in the container.

9. The apparatus of claim 8, wherein the means for measuring fluid in the container includes a balance for weighing the fluid in the container.

10. The apparatus of claim 8, wherein the means for measuring fluid in the container is effective to measure and/or monitor a change in the fluid content in the container over a desired time period.

11. The apparatus of claim 1, wherein the sheet is cellulosic.

12. The apparatus of claim 1, wherein the sheet is a fabric.

13. The apparatus of claim 1, further comprising a means for increasing vapor transport at the upper surface of the sheet.

14. The apparatus of claim 1, wherein the fluid-conveying lumen extends from the container to a plurality of terminal openings facing the lower surface of the sheet.

15. The apparatus of claim 14, wherein the openings are substantially identical in size.

16. The apparatus of claim 14, further comprising a means for transporting fluid through the conduit at a predetermined rate.

17. The apparatus of claim 1, further comprising the sheet and a weight having substantially coplanar lower exterior and interior surfaces in contact with the upper surface of the sheet.

18. The apparatus of claim 17, wherein the lower surfaces of the weight are substantially concentric about an axis perpendicular to the plane of the lower surfaces.

19. The apparatus of claim 1, further comprising a means for positioning an interfacing portion of the sheet through the support to absorb liquid upward against gravity.

20. An apparatus for transporting fluid to a sheet having an upper surface and a lower surface in a horizontal orientation, comprising:

a support structure having an upper surface supporting the sheet;

a container holding a fluid;

a conduit having a fluid-conveying lumen that extends from the container to an opening below the support structure and facing the lower surface of the sheet; and a means for positioning an interfacing portion of the sheet to absorb fluid through the opening against gravity.

21. The apparatus of claim 20, wherein the positioning means comprises one or more members for controllably pressing the interfacing portion of the sheet through the opening.

22. The apparatus of claim 21, wherein the fluid-conveying lumen extends from the container to a single opening below the support structure and the positioning means comprises one member for controllably pressing the interfacing portion of the sheet through the opening.

23. The apparatus of claim 22, further comprising a weight for having a lower surface in contact with the upper surface of the sheet, wherein the member includes a spiral grooves that allows for controllable positioning of the member relative to the weight and for controllably pressing the interfacing portion of the sheet through the opening.

24. The apparatus of claim 20, wherein the opening is located at least one millimeter below the support structure.

* * * * *